(12) United States Patent
Luo et al.

(10) Patent No.: US 12,419,677 B2
(45) Date of Patent: Sep. 23, 2025

(54) HIGH AND LOW TEMPERATURE COMPOSITE ABLATION SURGERY SYSTEM

(71) Applicant: HYGEA MEDICAL TECHNOLOGY CO., LTD., Beijing (CN)

(72) Inventors: Fuliang Luo, Beijing (CN); Cuihu Liu, Beijing (CN); Bowei Chen, Beijing (CN); Wensheng Wei, Beijing (CN); Jian Xiao, Beijing (CN); Jingjing Yang, Beijing (CN)

(73) Assignee: HYGEA MEDICAL TECHNOLOGY CO., LTD., Beijing (CN)

( * ) Notice: Subject to any disclaimer, the term of this patent is extended or adjusted under 35 U.S.C. 154(b) by 734 days.

(21) Appl. No.: 17/799,471

(22) PCT Filed: Dec. 13, 2019

(86) PCT No.: PCT/CN2019/125018
§ 371 (c)(1),
(2) Date: Aug. 12, 2022

(87) PCT Pub. No.: WO2021/109206
PCT Pub. Date: Jun. 10, 2021

(65) Prior Publication Data
US 2023/0338076 A1    Oct. 26, 2023

(30) Foreign Application Priority Data
Dec. 4, 2019    (CN) .......................... 201911229554.8

(51) Int. Cl.
*A61B 18/02*    (2006.01)
*A61B 18/04*    (2006.01)
*A61B 18/00*    (2006.01)

(52) U.S. Cl.
CPC .............. *A61B 18/02* (2013.01); *A61B 18/04* (2013.01); *A61B 2018/00577* (2013.01); *A61B 2018/0293* (2013.01); *A61B 2018/046* (2013.01)

(58) Field of Classification Search
CPC . A61B 18/02; A61B 18/04; A61B 2018/0262; A61B 2018/0293; A61B 2018/046
See application file for complete search history.

(56) References Cited

U.S. PATENT DOCUMENTS 3,398,738 A * 8/1968 Lamb ..................... A61B 18/02
128/DIG. 14
5,860,971 A * 1/1999 Clarke .................. A61B 18/02
606/22

(Continued)

FOREIGN PATENT DOCUMENTS

CN    101578073 A    11/2009
CN    109620392 A    4/2019

OTHER PUBLICATIONS

International Search Report of PCT Patent Application No. PCT/CN2019/125018 issued on Aug. 27, 2020.

*Primary Examiner* — Daniel W Fowler

(57) ABSTRACT

A high and low temperature composite ablation surgery system, relating to the technical field of cryotherapy, used to improve the safety and effectiveness of therapy, and comprising a main unit (100) and a cryogenic-thermal ablation probe (200) connected to the main unit (100). The main unit (100) comprises a cold working medium supply system (300), a hot working medium supply system (400), and a working medium distribution system (500). The working medium distribution system (500) can respectively control the cold working medium supply system (300) to deliver a cold working medium to the cryogenic-thermal ablation probe (200) and control the hot working medium supply (Continued)

system (400) to deliver a hot working medium to the cryogenic-thermal ablation probe (200). Therefore, after low-temperature therapy is completed, a therapy area can be quickly rewarmed, thereby providing a basis for improving the safety, economy and convenience of the surgery.

10 Claims, 16 Drawing Sheets

(56) References Cited

U.S. PATENT DOCUMENTS

| | | | | | |
|---|---|---|---|---|---|
| 6,014,864 | A | * | 1/2000 | Owen | F28F 13/00 |
| | | | | | 62/51.1 |
| 6,635,053 | B1 | * | 10/2003 | Lalonde | A61B 18/02 |
| | | | | | 606/22 |
| 2004/0082943 | A1 | * | 4/2004 | Littrup | A61B 18/02 |
| | | | | | 606/21 |
| 2004/0211193 | A1 | * | 10/2004 | Van der Walt | F25B 9/006 |
| | | | | | 62/62 |
| 2005/0261753 | A1 | * | 11/2005 | Littrup | F25B 9/02 |
| | | | | | 607/96 |
| 2008/0114344 | A1 | * | 5/2008 | Xiao | A61B 18/02 |
| | | | | | 606/20 |
| 2009/0270851 | A1 | * | 10/2009 | Babkin | A61B 18/02 |
| | | | | | 606/24 |
| 2010/0057064 | A1 | * | 3/2010 | Baust | A61B 18/02 |
| | | | | | 606/23 |
| 2010/0145160 | A1 | * | 6/2010 | Cinqualbre | A61L 2/0088 |
| | | | | | 600/300 |
| 2011/0245821 | A1 | * | 10/2011 | Zachman | A61B 18/02 |
| | | | | | 606/21 |
| 2014/0163538 | A1 | * | 6/2014 | Ryba | A61F 7/0085 |
| | | | | | 606/21 |
| 2017/0333122 | A1 | * | 11/2017 | Rajagopalan | A61M 29/02 |

* cited by examiner

HIGH AND LOW TEMPERATURE COMPOSITE ABLATION SURGERY SYSTEM

CROSS-REFERENCE TO RELATED APPLICATIONS

This application claims the priority of Chinese patent application CN201911229554.8, entitled "High and Low Temperature Composite Ablation Surgery System" and filed on Dec. 4, 2019, the entirety of which is incorporated herein by reference.

FIELD OF THE INVENTION

The present disclosure relates to the technical field of cryotherapy, and in particular, to a high and low temperature composite ablation surgery system.

BACKGROUND OF THE INVENTION

At present, the cryotherapy technology has gradually become the primary means of interventional tumor therapy. This technology relates to the physical therapy only, and has advantages, such as definite therapy effects, causing no spreading of cancer cells, the therapy process being minimally invasive and painless, quick recovery, causing no injury to normal tissues, relative to chemoradiotherapy. Clinical data shows that, for a patient treated with the cryotherapy technology, immune functions of the body is clearly enhanced, and the long-term survival rate is distinctly improved. The cryotherapy technology has apparent advantages in treating solid tumor, such as lung cancer, liver cancer, breast cancer, kidney cancer, prostate cancer, and the like.

The principles of the cryotherapy are as follows:
1. ice crystal growth and cell dehydration cause mechanical injuries to tumor cells;
2. blood embolization results in death of tumor tissues because of oxygen deficiency;
3. reversible injuries lead to apoptosis; and
4. freezing can stimulate immune adjustment, so as to produce a waterfall ectopic tumor inhibition effect.

In existing technologies, typical cryotherapy apparatuses are represented by the Cryocare Surgical System developed by Endocare, and the VISUAL-ICE Cryoablation System developed by Galil. The cryotherapy is achieved by the principle of the Joule-Thomson effect (i.e., the temperature change caused after a gas is forced through a porous plug and expands). When low-temperature ablation is performed, the temperature may be as low as −150° C. to −160° C., and when rewarming is performed, the temperature may be as high as 40° C. It is not difficult to found out that, the above cryotherapy apparatuses all possess one cooling principle, and the working temperature zone, limited by the cooling principle and properties of the working medium itself, can only provide a single-function therapy. Besides, limited by the working mechanism thereof, such cryotherapy apparatuses have a relatively high working pressure (12 MPa to 22 MPa), have potential safety hazards, and produce relatively loud noises; and working mediums used are relatively expensive; and in addition, it is required to connect the cryotherapy apparatuses to a high-pressure argon cylinder and a high-pressure helium cylinder during a surgery, and it is not convenient to use the cryotherapy apparatuses in the operating room with limited space. So far, there is no full-function type high and low temperature therapy apparatuses with a wide temperature range.

SUMMARY OF THE INVENTION

The present disclosure provides a high and low temperature composite ablation surgery system, which can incorporate a high intensity thermal ablation on the premise of satisfying requirements of a basic cryotherapy function and provide a basis for improving the safety, economy and convenience of a surgery.

The disclosure provides a high and low temperature composite ablation surgery system, including a main unit and a cryogenic-thermal ablation probe connected to the main unit. The cryogenic-thermal ablation probe is configured to perform therapy on a focus portion of a patient; and the main unit includes:
a cold working medium supply system, which is configured to deliver a cold working medium to the cryogenic-thermal ablation probe;
a hot working medium supply system, which is configured to deliver a hot working medium to the cryogenic-thermal ablation probe; and
a working medium distribution system, which is connected to the cold working medium supply system and the hot working medium supply system respectively, and is configured to control the cold working medium supply system to deliver the cold working medium to the cryogenic-thermal ablation probe or control the hot working medium supply system to deliver the hot working medium to the cryogenic-thermal ablation probe.

In an embodiment, the working medium distribution system includes:
a phase separator, which is connected to the cold working medium supply system; and
a precooler, which is provided with a gas channel and a liquid channel, a feeding side of the gas channel being in communication with a gas outlet end of the phase separator, a feeding side and a discharging side of the liquid channel are respectively in communication with a liquid outlet end of the phase separator and the cryogenic-thermal ablation probe,
wherein gas in the gas channel is used to precool liquid in the liquid channel.

In an embodiment, the gas channel is configured to be a channel having a maze shape.

In an embodiment, the main unit further includes a recycling system which is connected to a discharging port of the cryogenic-thermal ablation probe. The recycling system is connected to the cold working medium supply system and the hot working medium supply system respectively for collecting the cold working medium or the hot working medium after the therapy is performed or collecting the cold working medium discharged from the cold working medium supply system or the hot working medium discharged from the hot working medium supply system due to overpressure.

In an embodiment, the recycling system includes a heat exchanger. The heat exchanger is connected to the discharging end of the cryogenic-thermal ablation probe, and the heat exchanger is configured to warm the cold working medium discharged by the cryogenic-thermal ablation probe and discharge the cold working medium warmed to atmosphere, or cool the hot working medium discharged by the cryogenic-thermal ablation probe and recycle the hot working medium cooled.

In an embodiment, the cold working medium supply system includes a cold tank for bearing the cold working medium. The cold tank is configured to deliver the cold working medium under pressure to the cryogenic-thermal ablation probe.

In an embodiment, the cold tank is connected with a pressurization pipeline. The pressurization pipeline is configured to allow the cold working medium in the cold tank to realize self-pressurization.

In an embodiment, the hot working medium supply system includes a hot tank for bearing the hot working medium. The hot tank is configured to deliver the hot working medium under pressure to the cryogenic-thermal ablation probe.

In an embodiment, the hot tank is provided with a heating device. The heating device is configured to vaporize and pressurize the working medium in the hot tank.

In an embodiment, the main unit further includes an electrical control system and an interaction system which are electrically connected. The electrical control system is electrically connected to the cold working medium supply system, the hot working medium supply system and the working medium distribution system respectively, so as to control a working process of the working medium.

Compared with the existing technologies, the disclosure has the following advantages. The working medium distribution system can respectively control the cold working medium supply system to deliver a cold working medium to the cryogenic-thermal ablation probe or control the hot working medium supply system to deliver a hot working medium to the cryogenic-thermal ablation probe. Therefore, after low-temperature therapy is completed, a therapy area can be quickly rewarmed, thereby providing a basis for improving the safety, economy and convenience of the surgery.

BRIEF DESCRIPTION OF THE DRAWINGS

The disclosure will be described in a more detailed way below based on embodiments and with reference to the accompanying drawings.

LIST OF REFERENCE NUMERALS

100—main unit;
200—cryogenic—thermal ablation probe; 201—working medium feeding pipe; 202—working medium backflow pipe; 203—vacuum pipe; 204—vacuum layer;
300—cold working medium supply system; 400—hot working medium supply system; 500—working medium distribution system; 600—recycling system; 700—electrical control system; 800—interaction system;
210—probe delivery pipe; 220—temperature measurement probe;
310—cold working medium automatic perfusion system; 320—cold working medium pressure control system;
311—cold working medium storage tank; 312—discharging valve; 313—interface detection switch; 314—perfusion interface; 315—liquid adding valve; 316—one-way valve;
321—cold tank; 322—pressurization pipeline; 323—pressurization valve; 324,426—pressure sensor; 325, 425—safety valve; 326—liquid adding and gas releasing valve; 327,428,512—manually operated valve; 328—gas releasing valve; 329,427—pressure gauge; 330,430—liquid level indicator; 331—filter;
410—hot working medium automatic perfusion system; 420—hot working medium pressure control system;
411—hot working medium storage tank; 412—liquid adding opening; 413—perfusion pump; 414—perfusion valve;
421—hot tank; 422, 513—temperature sensor; 423—temperature switch; 424—heater; 429—gas releasing valve;
510—phase separator; 511—phase separation valve;
520—precooler; 521—gas channel; 522—upper plate; 523—lower plate;
610—heat exchanger; 611—fin; 612—air blower; 613—PTC heater; 620—recycling tank; 621—weighing sensor;
810—displayer; 820—function keyboard;
900—power assisting system; 910—housing; 911—power assisting wheel; 912—electrically controlled wheel; 913—handle; 914—wireless pad; 915—emergency stop button; 916—discharging port.

DETAILED DESCRIPTION OF THE EMBODIMENTS

The disclosure is further described with reference to the accompanying drawings.

Figure 1:
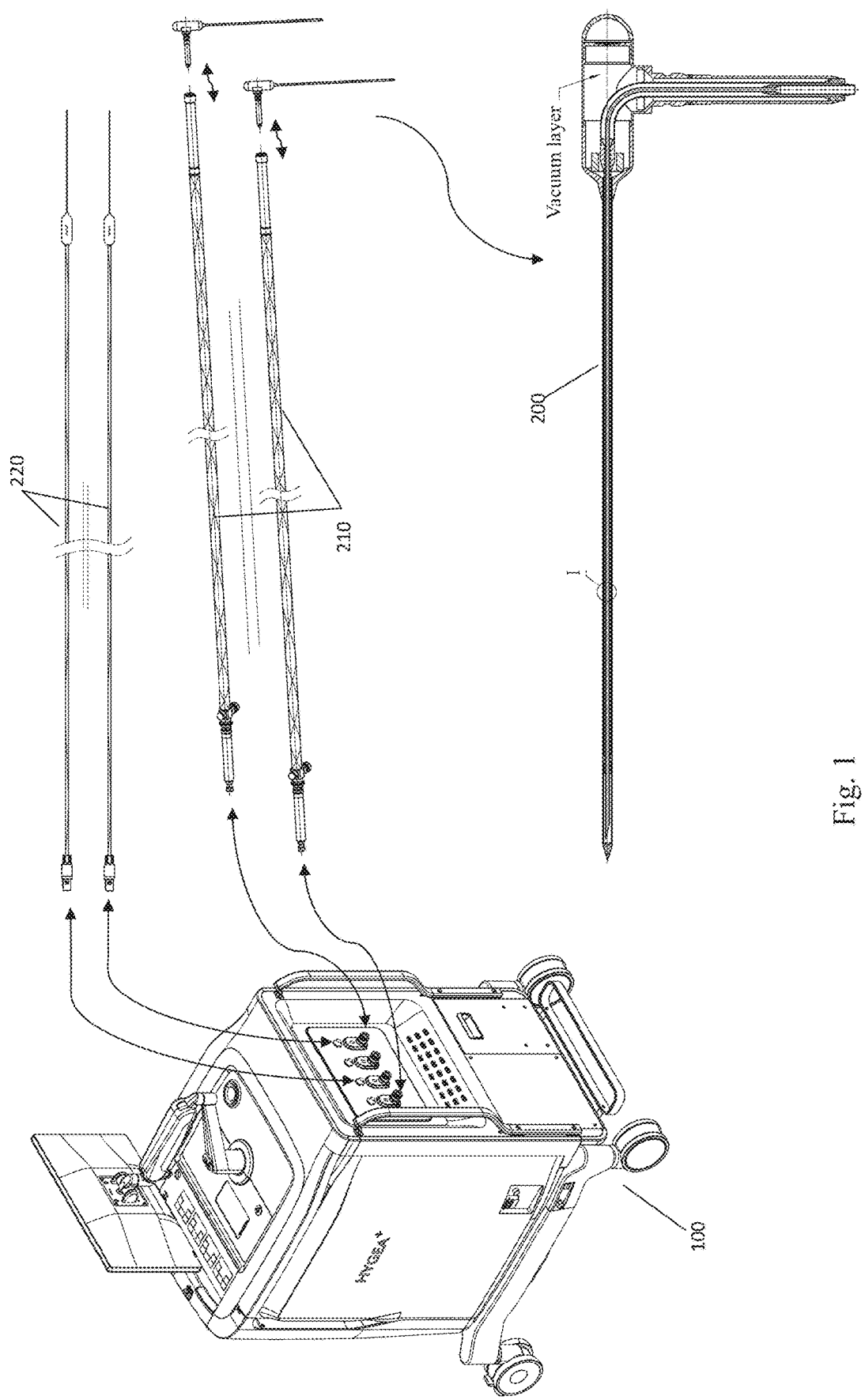
FIG. 1 schematically shows a structure of a high and low temperature composite ablation surgery system according to an embodiment of the disclosure.

As shown in FIG. 1, the disclosure provides a high and low temperature composite ablation surgery system, which includes a main unit 100 and a cryogenic-thermal ablation probe 200 connected to the main unit 100. The cryogenic-thermal ablation probe 200 is configured to perform therapy on a focus portion of a patient.

The main unit 100 includes a cold working medium supply system 300, a hot working medium supply system 400, and a working medium distribution system 500.

Specifically, the cold working medium supply system 300 is configured to deliver a cold working medium to the cryogenic-thermal ablation probe 200; the hot working medium supply system 400 is configured to deliver a hot working medium to the cryogenic-thermal ablation probe 200; and the working medium distribution system 500 is connected to the cold working medium supply system 300 and the hot working medium supply system 400 respectively, and is configured to control the cold working medium supply system 300 to deliver the cold working medium to the cryogenic-thermal ablation probe 200 or control the hot working medium supply system 400 to deliver the hot working medium to the cryogenic-thermal ablation probe 200.

The high and low temperature composite ablation surgery system provided in the disclosure shows a cryogenic cooling function and a rewarming function in clinical practice. Two stages of therapy are included, i.e., a cryotherapy stage and a rewarming stage. Specifically, at the cryotherapy stage, the cryogenic-thermal ablation probe 200 is inserted into the focus portion of the patient, and the cold working medium is delivered to the cryogenic-thermal ablation probe 200 through the cold working medium supply system 300. The cold working medium quickly passes through the ablation probe and evaporates by absorption of heat, and a great deal of cold energy is instantaneously supplied to pathological tissues to rapidly freeze and damage the tissues to achieve a therapy goal. After the cryotherapy stage is completed, the hot working medium is delivered to the cryogenic-thermal ablation probe 200 through the hot working medium supply system 400, and high-temperature hot-medium vapor reaches a therapy position of the cryogenic-thermal ablation probe 200 to instantaneously release a great deal of heat, so as to quickly rewarm a therapy area.

The cold working medium described in the disclosure may be a single substance, such as liquid nitrogen (with a boiling point of −196° C. under normal pressure), liquid oxygen (with a boiling point of −183° C. under normal pressure), liquid methane (with a boiling point of −161° C. under normal pressure), liquid argon (with a boiling point of −186° C. under normal pressure), liquid neon (with a boiling point of −246° C. under normal pressure), liquid helium (with a boiling point of −269° C. under normal pressure), liquefied nitrous oxide (with a boiling point of −88.5° C. under normal pressure), liquefied carbon dioxide (with a boiling point of −79° C. under normal pressure), and Freon 22 (with a boiling point of −50° C. under normal pressure), or may also be a mixture of the above substances.

The hot working medium described in the disclosure may be a single substance, such as water vapor (with a boiling point of 100° C. under normal pressure), methanol vapor (with a boiling point of 64.7° C. under normal pressure), formic acid vapor (with a boiling point of 100.8° C. under normal pressure), ethanol vapor (with a boiling point of 78° C. under normal pressure), ethanoic acid vapor (with a boiling point of 117.9° C. under normal pressure), ethyl ester vapor (with a boiling point of 54.3° C. under normal pressure), propanol vapor (with a boiling point of 82.5° C. under normal pressure), propionic acid vapor (with a boiling point of 141.1° C. under normal pressure), and propyl ester vapor (with a boiling point of 101.6° C. under normal pressure), and may also be a mixture of the above substances. It should be noted that the above temperature of the boiling point does not represent a rewarming temperature. In some embodiment, for example, a manner of vapor pressurization is used provide power to deliver the hot working medium to the cryogenic-thermal ablation probe 200, and a therapy temperature of the cryogenic-thermal ablation probe 200 may be higher than a boiling point of a selected hot working medium.

Therefore, the cold working medium and the hot working medium in the disclosure have wide sources, have low costs, and cover a broader temperature range, so as to provide a basis for improving the safety, economy and convenience of the surgery.

In addition, respective pipelines for delivering the cold working medium or the hot working medium are all provided with a heat insulation part, to ensure that a sufficient amount of the cold working medium is delivered to a probe tip of the cryogenic-thermal ablation probe 200.

Respective parts of the high and low temperature composite ablation surgery system are described individually below.

(I) Cold Working Medium Supply System 300

Figure 2:
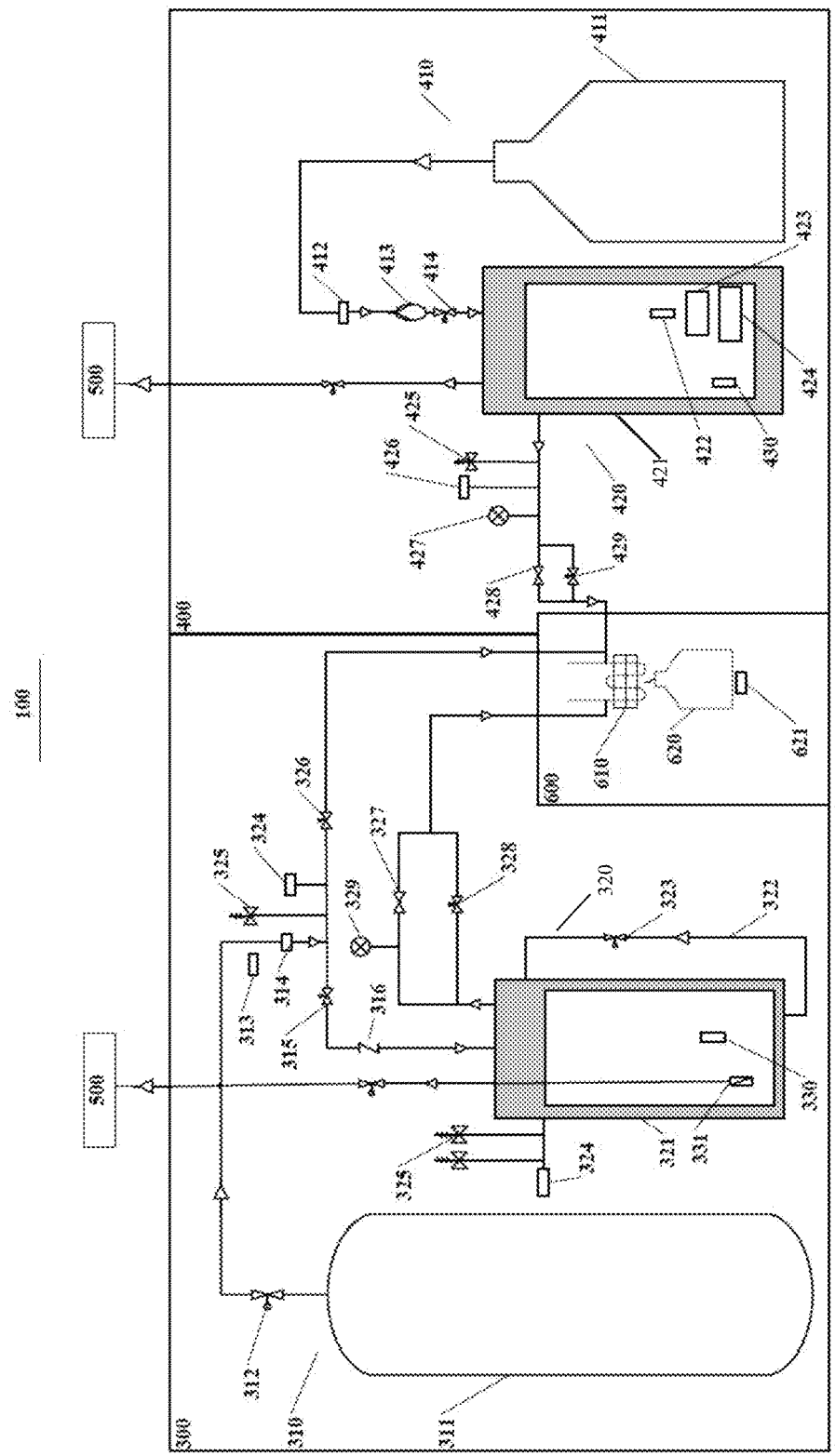
FIG. 2 schematically shows connection of a cold working medium supply system and a hot working medium supply system according to an embodiment of the disclosure.
Figure 3:
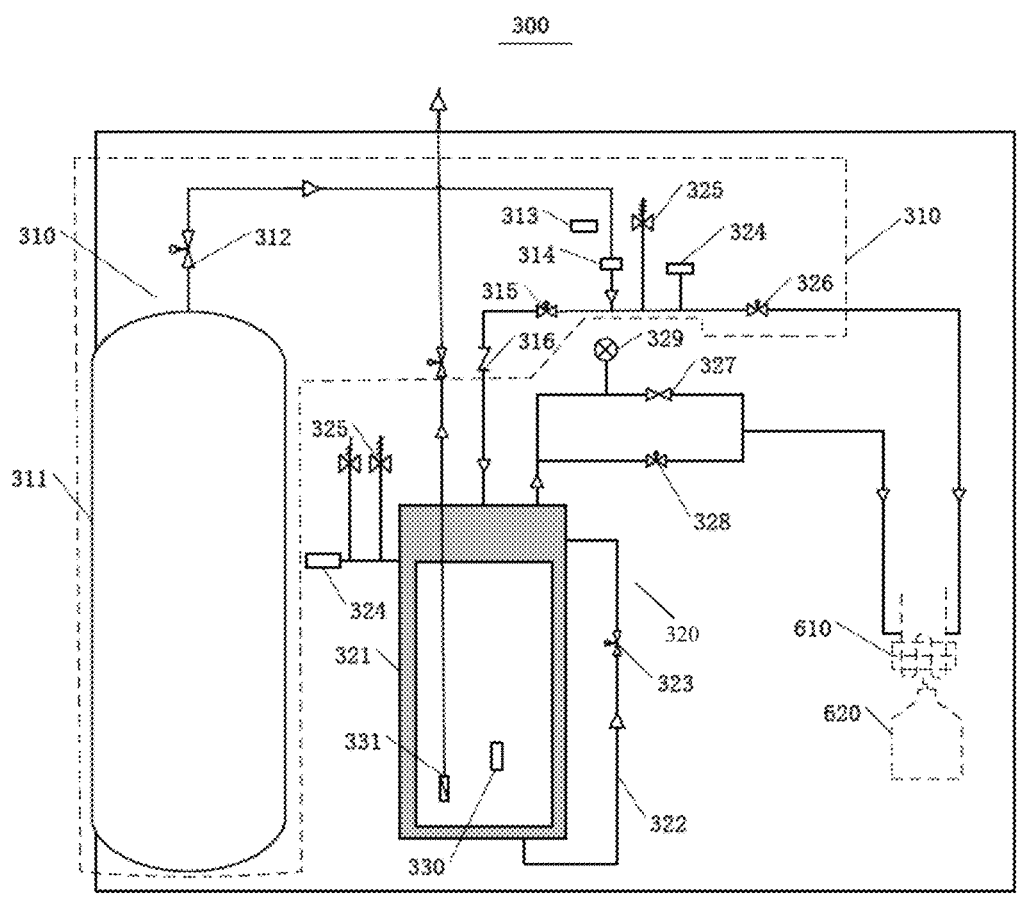
FIG. 3 schematically shows connection of the cold working medium supply system according to an embodiment of the disclosure.

As shown in FIGS. 2 and 3, the cold working medium supply system 300 includes a cold working medium automatic perfusion system 310 and a cold working medium pressure control system 320.

Specifically, the cold working medium automatic perfusion system 310 includes a cold working medium storage tank 311 for storing the cold working medium, and the cold working medium pressure control system 320 includes a cold tank 321 for delivering the cold working medium to the cryogenic-thermal ablation probe 200. The cold working medium storage tank 311 and the cold tank 321 are connected by a pipeline, so as to deliver the cold working medium in the cold working medium storage tank 311 to the cold tank 321.

On the pipeline for connecting the cold working medium storage tank 311 and the cold tank 321, a discharging valve 312, an interface detection switch 313, and a perfusion interface 314 are provided sequentially. The interface detection switch 313 is configured to open or close the perfusion interface 314 so as to allow the cold working medium storage tank 311 and the cold tank 321 to be in communication with each other or not in communication with each other.

On a pipeline between the perfusion interface 314 and the cold tank 321, a liquid adding valve 315 and a one-way valve 316 are further provided sequentially, to prevent a backflow of the working medium.

The cold tank 321 can be configured to deliver the cold working medium under pressure to the cryogenic-thermal ablation probe 200. An optional manner is that, the cold tank 321 is connected with a pressurization pipeline 322, and the pressurization pipeline 322 is configured to allow the cold working medium in the cold tank 321 to realize self-pressurization.

Specifically, two ends of the pressurization pipeline 322 are respectively connected to the cold tank 321 so as to form a closed loop. The pressurization pipeline 322 is provided with a pressurization valve 323. When the pressurization valve 323 is opened, the working medium in the cold tank 321 enters the pressurization pipeline 322. The working medium vaporizes by heat exchanging with the outside through a pipeline wall and rapidly expands in volume, thereby realizing self-pressurization.

The cold tank 321 is a vacuum heat-insulation pressure container made of stainless steel.

Besides, there are some alternative embodiments to realize delivering of the cold working medium under pressure from the cold tank 321 to the cryogenic-thermal ablation probe 200. For example, pressurization is performed by using an air compressor to force air into the cold tank 321; pressurization is performed by filling a high-pressure gas whose boiling point is not higher than that of the working medium; or pressurization is performed by heating the cold working medium so as to vaporize the cold working medium.

In addition, another more direct manner to provide power is to use a low-temperature pump to pump the cold working medium in the cold tank 321, so as to adjust a mass flow rate of the cold working medium delivered by controlling a revolution speed or the power of the pump.

The cold tank 321 is further provided with a pressure sensor 324 and two safety valves 325, so as to detect a pressure of the cold tank 321 and avoid an excessively high pressure of the cold tank 321 by the safety valves 325. Certain redundancy can be ensured by providing two safety valves 325, so as to further improve reliability of the cold tank 321.

The cold tank 321 is further connected to a recycling system 600 described below.

Specifically, on a pipeline between the cold working medium automatic perfusion system 310 and the recycling system 600, a liquid adding and gas releasing valve 326, a pressure sensor 324, and a safety valve 325 are provided sequentially. The pressure sensor 324 is configured to detect a pressure in the pipeline, and overpressure protection is performed by the safety valve 325.

On a pipeline for releasing the pressure from the cold tank 321 to the recycling system 600, a manually operated valve 327 and a gas releasing valve 328 are provided in parallel. On a pipeline at which the manually operated valve 327 is located, a pressure gauge 329 is connected in series with the manually operated valve 327, so as to manually control the pressure in the pipeline by the pressure gauge 329 and the manually operated valve 327. A conventional pressure control valve in existing technologies may be adopted as the gas releasing valve 328, and when the gas releasing valve 328 malfunctions, the safety valve 325 performs an effective pressure relief.

A normally opened valve may be selected for both the liquid adding and gas releasing valve 326 and the gas releasing valve 328. That is, when an apparatus is powered down, the pressure relief is automatically enabled, so that the apparatus is in a safe state with no pressure.

During perfusion of the cold working medium from the cold working medium storage tank 311 to the cold tank 321, when the pressure in the pipeline exceeds a certain value, the pressure relief may be performed by the liquid adding and gas releasing valve 326; and if the liquid adding and gas releasing valve 326 malfunctions, the pressure relief may be performed by the safety valve 325, so as to ensure safety during the perfusion. In a case where both the pressure sensor 324 and the safety valve 325 malfunction, the pressure relief may also be performed by reading the pressure with the pressure gauge 329 and operating the manually operated valve 327 in time, so as to ensure safety of the apparatus.

Further, the cold tank 321 is provided therein with a liquid level indicator 330 for identifying a liquid level of the cold tank 321.

Furthermore, the cold tank 321 is provided, at a bottom of a discharging pipeline connecting to the working medium distribution system 500, with a filter 331, so as to avoid blocking caused by impurities entering the working medium distribution system 500 or a delivery pipeline, thereby improving the effectiveness of the therapy with the apparatus.

A working process of the cold working medium automatic perfusion system 310 is described in detail below.

Firstly, the cold working medium storage tank 311 and the perfusion interface 314 are connected. After it is detected by the interface detection switch 313 that connection of the perfusion interface 314 is completed, the liquid adding valve 315 is opened, and meanwhile the liquid adding and gas releasing valve 326 is closed.

Secondly, the discharging valve 312 of the cold working medium storage tank 311 is opened, and the cold working medium is injected to the cold tank 321 continually; when the liquid level indicator 330 detects that liquid adding of the cold working medium is completed, the liquid adding valve 315 is closed, and meanwhile the liquid adding and gas releasing valve 326 is opened, the discharging valve 312 of the cold working medium storage tank 311 being closed at the same time; and then the perfusion interface 314 is disconnected, so as to complete an operation of liquid adding.

A working process of the cold working medium pressure control system 320 is described in detail below.

When the apparatus is prepared to work, it is required to increase the pressure in the cold tank 321, so as to provide power to discharge the cold working medium for performing therapy.

Accordingly, firstly, the pressurization valve 323 is opened, and the working medium in the cold tank 321 enters the pressurization pipeline 322. The working medium vaporizes by heat exchanging with the outside through the pipeline wall and rapidly expands in volume, thereby realizing self-pressurization.

Secondly, in order to realize effectiveness and consistency of the therapy, it is required to perform precise control on the pressure of the cold working medium. Therefore, the pressure in the cold tank 321 is monitored in real time. When the pressure exceeds a working pressure, the pressure relief is performed by opening the gas releasing valve 328. In order to achieve a stable pressure, opening of the pressurization valve 323 and opening of the gas releasing valve 328 are controlled with different methods according to different strategies and working conditions.

An optional pressure control method is as follows. A working pressure is set to be P. When the pressure in the cold tank 321 is far less than P, the pressurization valve 323 is opened, and the gas releasing valve 328 is closed. When the pressure reaches P−ΔP0, the pressurization valve 323 is closed. After a certain time length, the current pressure is examined. If the current pressure has a relatively large difference from the set pressure P, the pressurization valve 323 is opened again. The above process is repeated so that the pressure gradually approximates the set pressure P.

Since heat leakage of the cold tank 321 necessarily exists, the pressure in the cold tank 321 also slowly increases. When the pressure reaches P+ΔP0, the gas releasing valve 328 is opened for performing the pressure relief and is closed when the pressure is released to reach P. A concurrent circumstance is that, with gradual consumption of the cold working medium in the therapy process, a gas-phase space in the cold tank 321 increases, and the pressure in the cold tank may also gradually decreases. Therefore, when the pressure is lower than P−ΔP1, it is required to open the pressurization valve 323 of the cold tank 321, and the pressurization valve 323 is closed when the pressure reaches P+ΔP1.

It is necessary to perform a large number of experiments to determine values of ΔP0 and ΔP1, and ΔP1 is less than ΔP0. In addition, the values of ΔP0 and ΔP1 are also associated with the liquid level of the cold tank 321, and thus a control strategy under different liquid levels may be adjusted according to needs.

(II) Hot Working Medium Supply System 400

Figure 4:
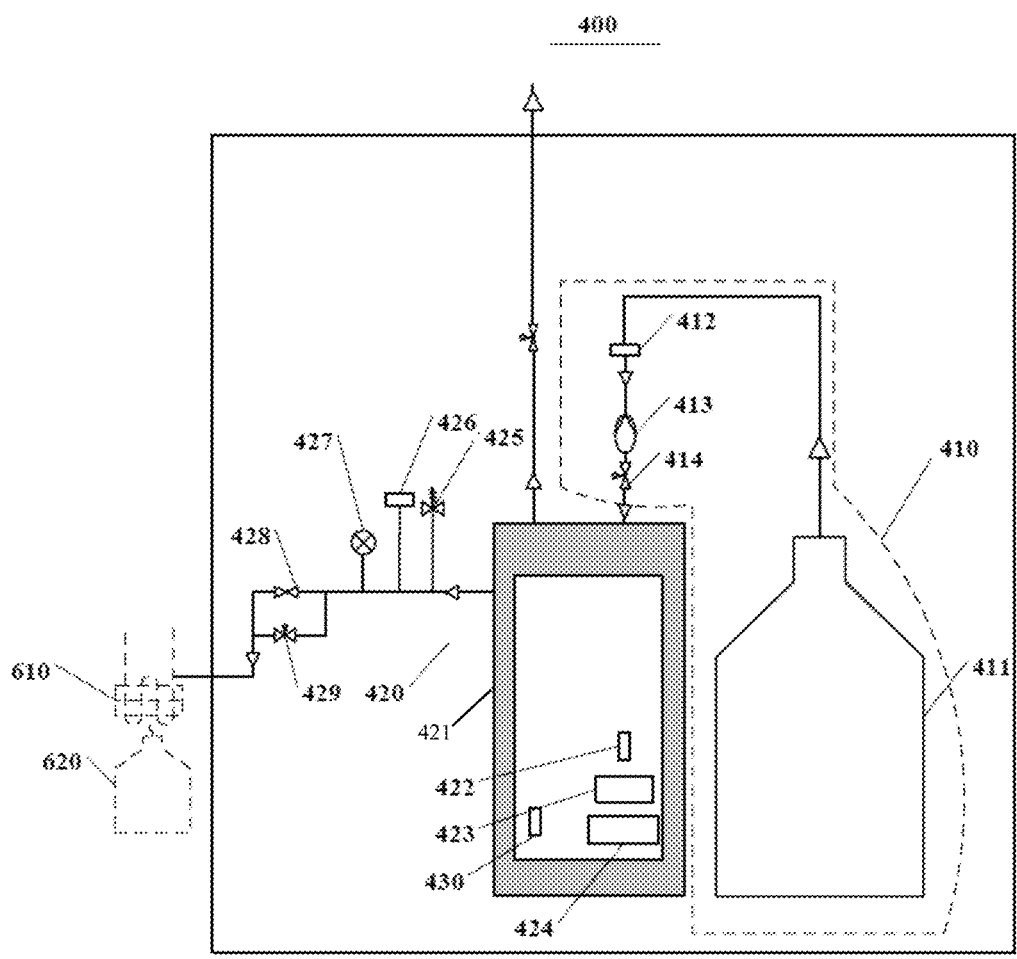
FIG. 4 schematically shows connection of the hot working medium supply system according to an embodiment of the disclosure.

As shown in FIGS. 2 and 4, the hot working medium supply system 400 includes a hot working medium automatic perfusion system 410 and a hot working medium pressure control system 420.

Specifically, the hot working medium automatic perfusion system 410 includes a hot working medium storage tank 411 for storing the hot working medium, and the hot working medium pressure control system 420 includes a hot tank 421 for delivering the hot working medium to the cryogenic-thermal ablation probe 200. The hot working medium storage tank 411 and the hot tank 421 are connected by a pipeline, so as to deliver the hot working medium in the hot working medium storage tank 411 to the hot tank 421.

On the pipeline for connecting the hot working medium storage tank 411 and the hot tank 421, a liquid adding opening 412, a perfusion pump 413, and a perfusion valve 414 are provided sequentially.

The hot tank 421 is configured to deliver the hot working medium under pressure to the cryogenic-thermal ablation probe 200. An optional manner is that, the hot tank 421 is heated, so that the hot working medium generates vapor, so that the pressure is increased. For example, a heating device, such as a heating rod and a heating plate, is provided in the hot tank 421; or ceramics which covers an internal cylinder of the hot tank 421 or an external wall of a delivery pipeline may be provided to perform heating; or manners, such as heating with a microwave which is used to directly heat the working medium, may be adopted.

In an embodiment illustrated in the disclosure, the hot tank 421 is provided therein with a temperature sensor 422, a temperature switch 423, and a heater 424. The hot working medium in the hot tank 421 is heated by the heater 424 for performing pressurization, and a temperature of the hot working medium is controlled by the temperature switch 423 and the temperature sensor 422. When there is excessively small amount of medium in the hot tank 421, if the heater 424 is working, the temperature switch 423 is disconnected when the temperature increases to an activation temperature of the temperature switch 423 to compulsively stop the heater 424 from working, which plays a role of dry heating prevention, thereby improving the safety of the apparatus.

In addition, the hot tank 421 is further provided therein with a liquid level indicator 430 (a liquid level sensor). In a process of automatic perfusion of the hot working medium from the hot working medium storage tank 411 to the hot tank 421, the liquid level indicator 430 monitors a liquid level of the hot tank 421 at any time. If the liquid level does not change within a period, an operator is reminded to change the hot working medium storage tank 411, so as to avoid that the perfusion pump 413 operates with nothing to pump and reduce abrasion.

The hot tank 421 is a vacuum heat-insulation pressure container made of stainless steel, which reduces heat leakage and improves the efficiency of the apparatus.

The hot tank 421 is further connected to the recycling system 600 described below.

On a pipeline between the hot tank 421 and the recycling system 600, a safety valve 425, a pressure sensor 426, a pressure gauge 427, and a manually operated valve 428 are provided sequentially in series. Besides, the manually operated valve 428 and a gas releasing valve 429 are connected in parallel.

The gas releasing valve 429 is a conventional pressure control valve, and when the gas releasing valve 429 malfunctions, the safety valve 425 performs an effective pressure relief. In a case where both the pressure sensor 426 and the safety valve 425 malfunction, the pressure relief may also be performed by reading the pressure with the pressure gauge 427 and operating the manually operated valve 428 in time, so as to ensure safety of the apparatus.

A working process of the hot working medium automatic perfusion system 410 is described in detail below.

Firstly, the hot working medium storage tank 411 and the liquid adding opening 412 are connected. An ordinary silicone hose may be used for performing connection.

Secondly, a liquid adding action is performed. The perfusion valve 414 is opened, and meanwhile the perfusion pump 413 is turned on, so that the hot working medium is injected to the hot tank 421 continually; when the liquid level indicator 430 detects that liquid adding of the hot working medium is completed, the perfusion valve 414 is closed, and the perfusion pump 413 is turned off; and then the liquid adding opening 412 is disconnected, so as to complete an action of liquid adding.

A working process of the hot working medium pressure control system 420 is described in detail below.

When the apparatus is prepared to work, it is required to increase the pressure in the hot tank 421, so as to provide power to discharge the hot working medium for performing therapy.

According to the above optional solution, the disclosure adopts a manner of heating for vaporization to increase the pressure in the hot tank 421, and an energy source for performing high-temperature therapy is hot vapor.

In order to realize effectiveness and consistency of the therapy, it is required to perform precise control on the pressure of the hot tank 421. Therefore, it is required to monitor the pressure in the hot tank 421 in real time. When the pressure exceeds a working pressure, the pressure relief is performed by opening the gas releasing valve 429. In order to achieve a stable pressure, turning-on of the heater 424 and opening of the gas releasing valve 429 are controlled with different methods according to different strategies and working conditions.

Since a saturated vapor pressure of the hot working medium is associated with the temperature, an optional control method is to adopt temperature PID adjustment to adjust the pressure.

(III) Working Medium Distribution System 500

As shown in FIGS. 5 to 7, FIG. 13, and FIG. 14, the working medium distribution system 500 includes a phase separator 510. In a process of delivering the cold working medium, the cold working medium gasifies due to heat exchanging with the outside through a pipeline wall. If the cold working medium delivered to the cryogenic-thermal ablation probe 200 includes a large proportion of gaseous cold working medium, the effect of cryotherapy is affected. Therefore, by using the phase separator 510, most of the cold working medium delivered to the cryogenic-thermal ablation probe 200 is in a liquid state.

Specifically, the cold tank 321 is connected to the phase separator 510 by a pipeline, and a lower end of the phase separator 510 is connected to the cryogenic-thermal ablation probe 200 by a pipeline. On a pipeline between an upper end of the phase separator 510 and the recycling system 600, a phase separation valve 511 and a manually operated valve 512 are provided sequentially. An aperture is provided at the upper end of the phase separator 510. Gasified cold working medium is discharged out of the system through the phase separation valve 511 and the manually operated valve 512, and the liquid working medium is fed into the cryogenic-thermal ablation probe 200 through valves, so as to realize the purpose of gas-liquid separation.

The manually operated valve 512 may also adjust flow resistance of the pipeline, so as to achieve a balance between liquid nitrogen consumption and gas-liquid separation.

A temperature sensor 513 is provided downstream of the phase separation valve 511. When all gaseous nitrogen passing through the phase separator 510 is discharged and liquid nitrogen is delivered, the phase separation valve 511 may be closed, so as to reduce loss of the liquid nitrogen at the phase separator 510.

The working medium distribution system 500 further includes a precooler 520 connected to the phase separator 510. The precooler 520 is provided with a gas channel 521 and a liquid channel A feeding side of the gas channel 521 is in communication with a gas outlet end of the phase separator 510, and a feeding side and a discharging side of the liquid channel are respectively in communication with a liquid outlet end of the phase separator 510 and the cryogenic-thermal ablation probe 200. Gas in the gas channel 521 is used to precool liquid in the liquid channel.

The gaseous working medium and the liquid working medium are separated by the phase separation valve 511. However, since the gaseous working medium also carries certain cold energy, if this portion of gaseous working medium is recycled or discharged directly, the cold energy is wasted. Therefore, the gaseous working medium is allowed to pass through the gas channel 521 of the precooler 520, and meanwhile the liquid working medium is allowed to pass through the liquid channel of the precooler. Since the gas channel 521 can cover at least a portion of the liquid channel, in flowing of the gaseous working medium and the liquid working medium, the cold energy of the gaseous working medium can be used to precool the liquid working medium, such that the liquid working medium fed into the cryogenic-thermal ablation probe 200 can obtain a lower treatment temperature.

Further, the gas channel 521 is configured to be a channel having a maze shape to increase a flowing path of the gas, so that the cold energy of gas can be utilized more adequately.

Figure 13:
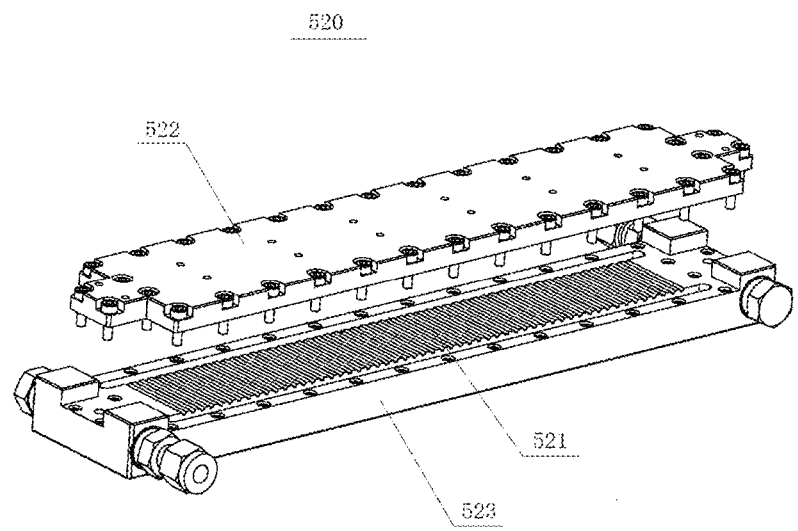
FIG. 13 schematically shows a structure of a precooler according to an embodiment of the disclosure.

Specifically, as shown in FIG. 13, the precooler 520 includes an upper plate 522 and a lower plate 523, which are connected by a locking screw. The upper plate 522 is provided thereon with a channel having a maze shape, i.e., the gas channel 521. The upper plate 522 and the lower plate 523 are provided with liquid channels. The gaseous working medium can play a role of cooling the upper plate 522 and the lower plate 523, so that the cold energy of the gaseous working medium is utilized to precool the liquid working medium, so as to improve the utilization efficiency of the cold working medium.

The liquid channels of the precooler 520 are provided with multiple discharging connectors (ferrule fittings), and thus discharging of respective channels can be controlled independently.

(IV) Recycling System 600

In the disclosure, the cold working medium or the hot working medium is fed into the cryogenic-thermal ablation probe 200. After the therapy ends, the cold working medium and the hot working medium can both be recycled through a discharging end of the cryogenic-thermal ablation probe 200. That is, recycling is performed through the recycling system 600.

Specifically, as shown in FIG. 2, the recycling system 600 includes a heat exchanger 610. The heat exchanger 610 is connected to the discharging end of the cryogenic-thermal ablation probe 200. The heat exchanger 610 is configured to warm the cold working medium discharged by the cryogenic-thermal ablation probe 200 and discharge the warmed cold working medium to atmosphere, or cool the hot working medium discharged by the cryogenic-thermal ablation probe 200 and recycle the cooled hot working medium.

The cold working medium or the hot working medium discharged from the discharging end of the cryogenic-thermal ablation probe 200 is fed into the heat exchanger 610 through a pipeline. With respect to the cold working medium, the heat exchanger 610 heats the cold working medium so as to increase the temperature of the cold working medium, thereby avoiding generation of too much condensed white fog. With respect to the hot working medium, heat exchanging with the air is performed through a fin 611 of the heat exchanger 610 to condense vapor of the hot working medium, thereby avoid spreading of the vapor in the environment.

Figure 14:
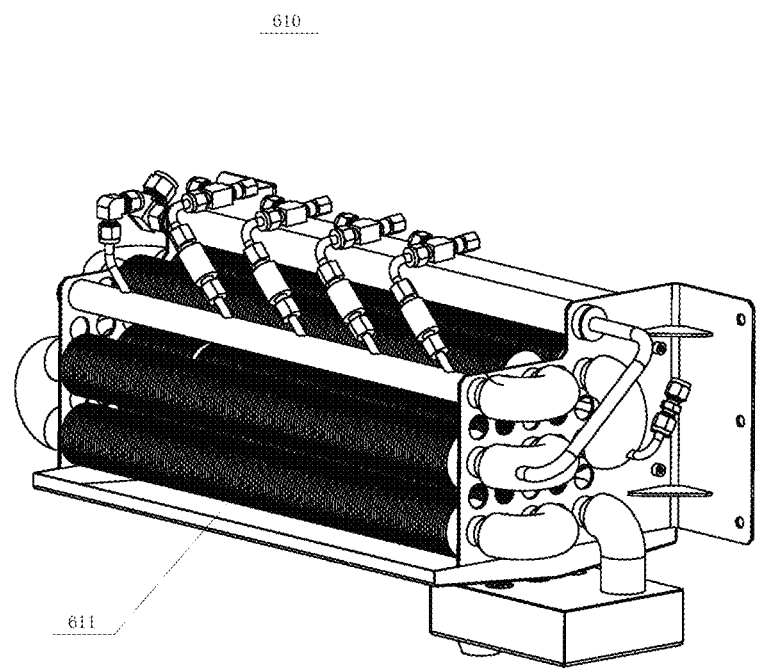
FIG. 14 and FIG. 15 schematically show a structure of a heat exchanger according to an embodiment of the disclosure.
Figure 15:
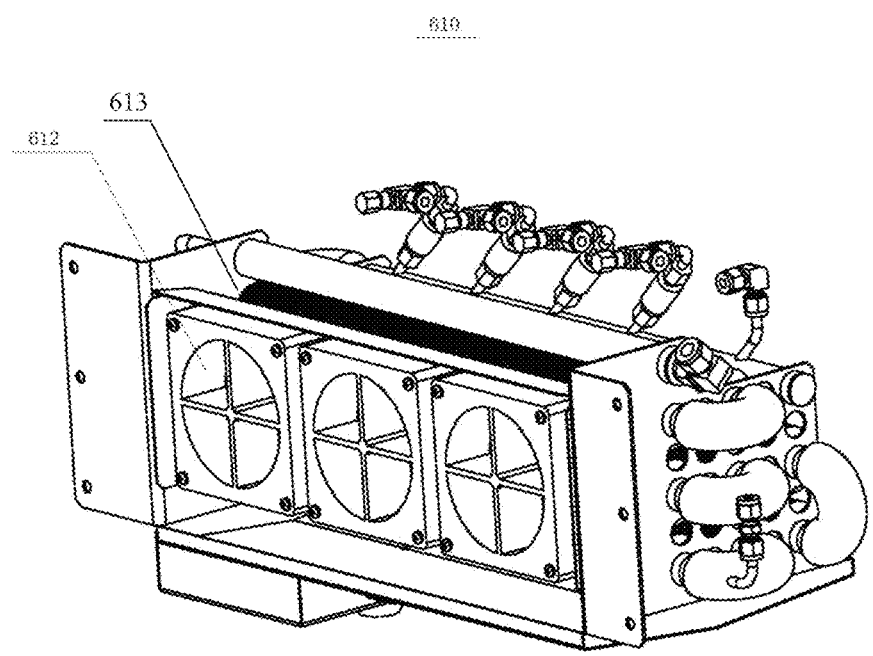

As shown in FIGS. 14 and 15, the heat exchanger 610 is an air-cooled heat exchanger. A cold wind is blown to the fin 611 by an air blower 612 to condense the vapor of the hot working medium. The air-cooled heat exchanger is integrated with a PTC heater 613. The PTC heater 613 adopts a U-shaped corrugate radiating fin, which can improve the heat dissipation rate thereof. Moreover, advantages of gluing and the mechanical type are combined, and various thermal and electric phenomena when the PTC heater 613 operates are fully considered. The PTC heater 613 has a strong binding force, excellent thermal conduction and heat dissipation properties, and high efficiency, and is safe and reliable.

Besides, such a PTC heater 613 has advantages of small thermal resistance and high heat exchanging efficiency, and is an electric heater which has an automatic constant temperature and saves electricity. An outstanding feature of the PTC heater 613 lies in its safety performance That is, when the air blower malfunctions and stops to rotate, the power of the PTC heater 613 drops automatically and rapidly because adequate heat dissipation cannot be performed. At this time, a surface temperature of the heater is maintained around the Curie temperature (which is normally about 250° C.), and thus, a "red" phenomenon on a surface of the heater, such as a tubular electric heating element, is not caused, which greatly improves the heat exchanging efficiency and has high safety.

Meanwhile, the cold working medium discharged from the cold working medium supply system 300 due to overpressure or the hot working medium discharged from the hot working medium supply system 400 due to overpressure may be fed into the heat exchanger 610 for recycling treatment.

The recycling system 600 further includes a recycling tank 620 provided below the heat exchanger 610. Heat exchanging with the air is performed through the fin of the heat exchanger 610 to condense the vapor of the hot working medium, and the condensed hot working medium enters the recycling tank 620 for recycling treatment.

A weighing sensor 621 is provided under the recycling tank 620. When the condensed hot working medium in the recycling tank 620 reaches a certain amount, the weighing sensor 621 sends an alarm to remind a user to take an action in time, so as to avoid spilling of the working medium.

(V) Electrical Control System 700 and Interaction System 800

As shown in FIGS. 8 to 13, the main unit 100 further includes an electrical control system 700 and an interaction system 800 which are electrically connected. The electrical control system 700 is electrically connected to the cold working medium supply system 300, the hot working medium supply system 400 and the working medium distribution system 500 respectively, so as to control a working process of the working medium.

The electrical control system 700 includes a power supply system and a computer control system. The power supply system includes an air switch, a filter, a soft start circuit, an isolation transformer, and a switching power supply, and is powered by a lithium battery. The computer control system is in communication with electrical equipment such as pressure sensors 324, 426, temperature sensors 422, 513, liquid level indicators 330, 430, and a weighting sensor 621, so as to collect signals of pressure, temperature, liquid level, weight, position, and the like. Besides, the computer control system is also in communication with switches of execution mechanisms, such as the valve, the pump, the heater 424, the air blower 612 described hereinabove.

The electrical control system 700 may be implemented by manners, such as PCBA or PLC.

The interaction system 800 includes a displayer (touch screen) 810, a function keyboard 820, and a wireless pad 914, which are provided at a housing 910, for performing surgical operations, and the displayer (touch screen) 810, the function keyboard 820, and the wireless pad 914 may all be operated independently. The interaction system 800 has functions, such as tri-color light indication, battery power indication, surgery discharging status indication, and RFID identification to help the user to better use the system, which improves usability of the system.

The interaction system 800 may be integrated with a 5G communication module. When the interaction system 800 is connected to the Internet, the manufacturer of the medical instrument may monitor a usage state of the system through an enterprise server, so as to collect data of those apparatuses that have been put on the market and provide conditions for maintenance and optimization of the apparatuses.

In addition, the housing 910 is further provided thereon with an emergency stop button 915.

The housing 910 is provided on a rear side with four discharging ports 916 which are respectively connected to the temperature measurement probe 220 and probe delivery pipe 210.

The main unit 100 further includes a power assisting system 900. The power assisting system 900 includes a power assisting wheel 911, an electrically controlled wheel 912, a lithium battery, and a handle 913, which are provided on the housing 910. The power assisting wheel 911 provides power for movement of the main unit 100. The electrically controlled wheel 912 is configured to automatically lock the housing 910 when the housing 910 stops. The handle 913 is integrated with a torque sensor, so that a nurse in the hospital can conveniently move the apparatus.

The above cold working medium supply system 300, the hot working medium supply system 400, the working medium distribution system 500, the recycling system 600, and the electrical control system 700 are all integrated in the housing 910, and the apparatus can be moved conveniently by using the power assisting system 900.

(VI) Cryogenic-Thermal Ablation Probe 200

As shown in FIG. 1, the cryogenic-thermal ablation probe 200 is connected to the cold working medium supply system 300 and the hot working medium supply system 400 via the probe delivery pipe 210. The probe delivery pipe 210 has a vacuum heat insulation layer, and thus an operator is not affected by the low temperature and the high temperature.

By using the probe delivery pipe 210, delivering and recycling of the working medium in the probe delivery pipe 210 can be realized. The probe delivery pipe 210 is soft, so that the operator can conveniently rotate and bend the probe delivery pipe 210 during use, which greatly improve operability in the surgery.

Further, connection between the probe delivery pipe 210 and the cryogenic-thermal ablation probe 200 and connection between the probe delivery pipe 210 and the cold working medium supply system 300 or the hot working medium supply system 400 are realized by quick insertion, which is convenient for the operator to perform an operation and confirm the connection so as to achieve firm connection.

The main unit 100 is further connected with a temperature measurement probe 220, which is configured to detect a temperature of tissues during the surgery. The temperature measurement probe 220 is provided in a probe tube thereof with a temperature sensor (for example, a T-type thermoelectric couple).

The probe tube of the temperature measurement probe 220 has a diameter of 0.5 mm to 3 mm. A leading wire of the temperature measurement probe 220 and the main unit 100 are connected by a coupling multi-core connector, which is convenient for plugging and unplugging, and there is also a loosening prevention design.

The cryogenic-thermal ablation probe 200 and the temperature measurement probe 220 are both disposable sterile products, are provided thereon with an electric encryption chip, which can be effectively identified by an RFID card reader of the interaction system 800 and is used in a limited time, so as to avoid repeated use of the disposable sterile products. Parameters, such as batch number, period of validity, specification, of the cryogenic-thermal ablation probe 200 or the temperature measurement probe 220 may also be recorded in the chip.

Besides, a diameter of the probe tube of the cryogenic-thermal ablation probe 200 is generally 1 mm to 8 mm.

Figure 16:
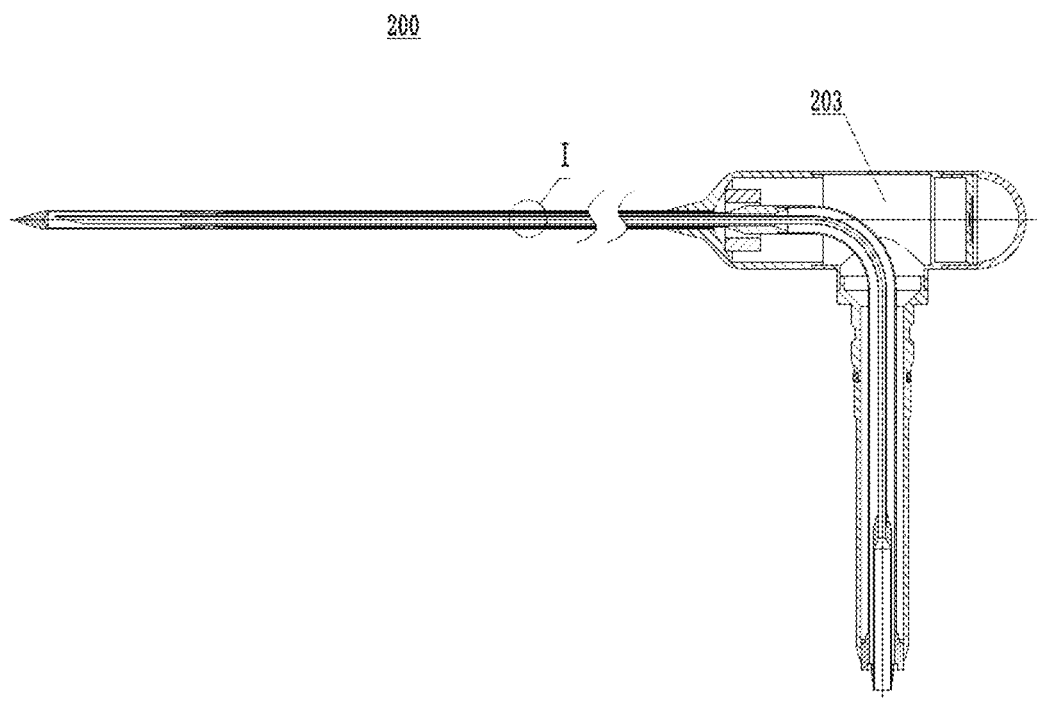
FIG. 16 schematically shows a structure of a cryogenic-thermal ablation probe according to an embodiment of the disclosure.
Figure 17:
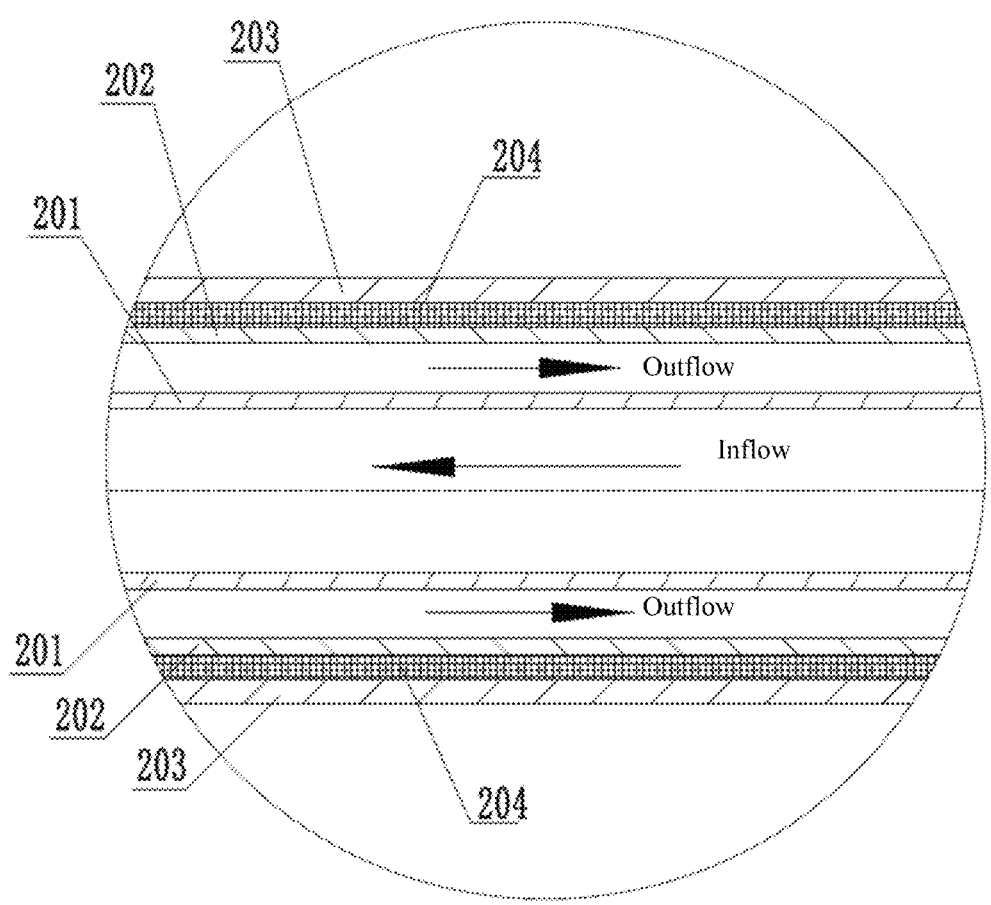
FIG. 17 is an enlarged view of FIG. 16 at a position of I.

Specifically, as shown in FIGS. 16 and 17, the cryogenic-thermal ablation probe 200 includes a working medium feeding pipe 201 and a working medium backflow pipe 202 sleeved outside the working medium feeding pipe 201. The working medium feeding pipe 201 may be connected to the cold working medium supply system 300 or the hot working medium supply system 400 respectively, and the cold working medium or the hot working medium may be fed into the working medium feeding pipe 201 (a flowing direction when the working medium is fed is shown by an arrow in FIG. 17) through the cold working medium supply system 300 or the hot working medium supply system 400.

When the cold working medium or the hot working medium in the working medium feeding pipe 201 reaches a probe tip position of the cryogenic-thermal ablation probe 200, therapy is performed on a therapy area. After the therapy is completed, the cold working medium or the hot working medium is discharged to the recycling system 600 along the working medium backflow pipe 202 (a flowing direction when the working medium is discharged is shown by an arrow in FIG. 17). That is, the flowing direction of the working medium in the working medium backflow pipe 202 and the flowing direction of the working medium in the working medium feeding pipe 201 are opposite.

Therefore, by a sleeve connection of the pipelines, the cryogenic-thermal ablation probe 200 in the disclosure can combine feeding (inflow) and discharging (backflow), and thus there is no need to provide an external connection pipe for the working medium feeding pipe 201 and the working medium backflow pipe 202 respectively, thereby greatly simplifying a structure of a connection pipeline and a structure of a medium storage apparatus.

Besides, both the working medium feeding pipe 201 and the working medium backflow pipe 202 are configured to have a bent pipe structure. That is, extension directions of both the working medium feeding pipe 201 and the working medium backflow pipe 202 are changed. As shown in FIG. 16, the cryogenic-thermal ablation probe 200 forms an L-shaped structure on the whole, and thus a size of the cryogenic-thermal ablation probe as a whole in one direction is not too large. In addition, above all, even there is a sudden disturbance or vibration acting on a handle position of the cryogenic-thermal ablation probe 200, the acting force is not immediately transferred to the probe tip position of the cryogenic-thermal ablation probe 200 to affect the patient. Therefore, the above-mentioned bent pipe structure can reduce the influence of unstable factors, such as the disturbance, on the probe tip position of the cryogenic-thermal ablation probe 200, thereby improving the therapy stability of the ablation probe 200.

Further, the cryogenic-thermal ablation probe 200 further includes a vacuum pipe 203. The vacuum pipe 203 is sleeved outside the working medium backflow pipe 202 and can cover at least a portion of an external wall of the working medium backflow pipe 202, so that a vacuum layer 204 is formed between at least a portion of the external wall of the working medium backflow pipe 202 and at least a portion of an internal wall of the vacuum pipe 203, as shown in FIG. 17. The vacuum layer 204 can better enable the cryogenic-thermal ablation probe 200 to have an excellent vacuum heat insulation property in a non-therapy portion (so as to prevent the non-therapy portion from causing freezing injuries to normal skin tissues of the human body or a surgery operator who touches the non-therapy portion of the ablation probe when the cryotherapy targets tissues).

Figure 5:
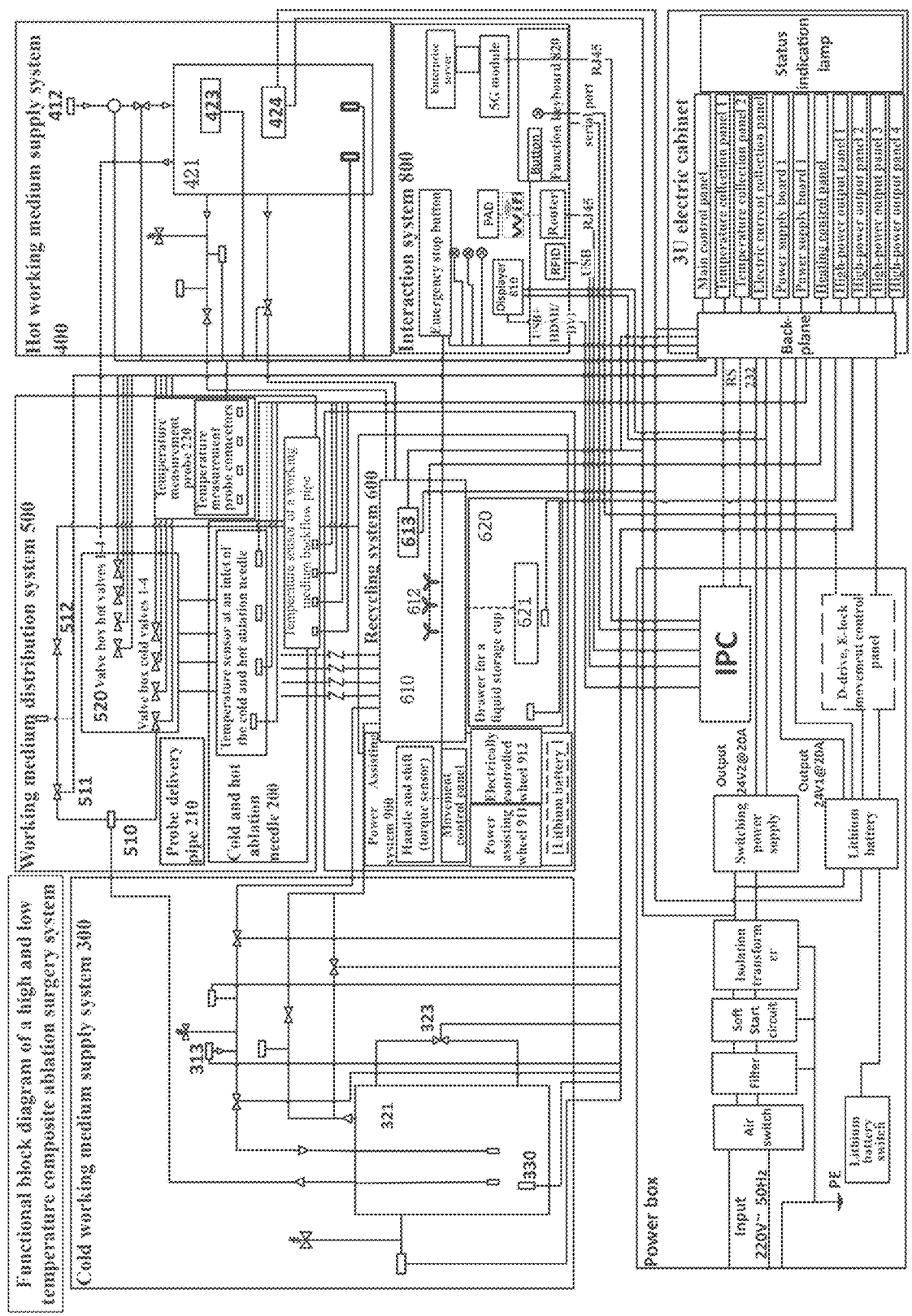
FIG. 5 shows a functional block diagram of a high and low temperature composite ablation surgery system according to an embodiment of the disclosure.
Figure 6:
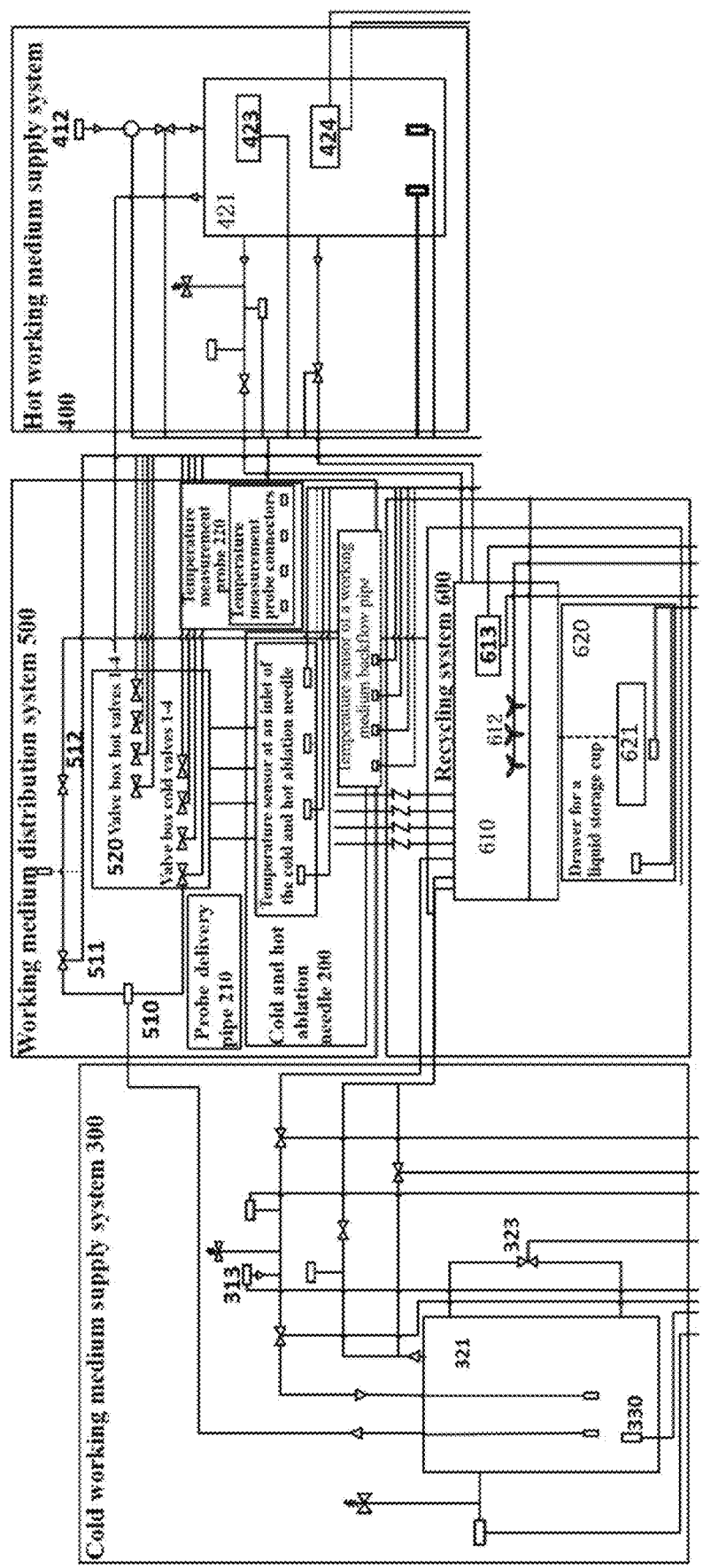
FIG. 6 and FIG. 7 schematically show connection of a working medium distribution system according to an embodiment of the disclosure.
Figure 7:
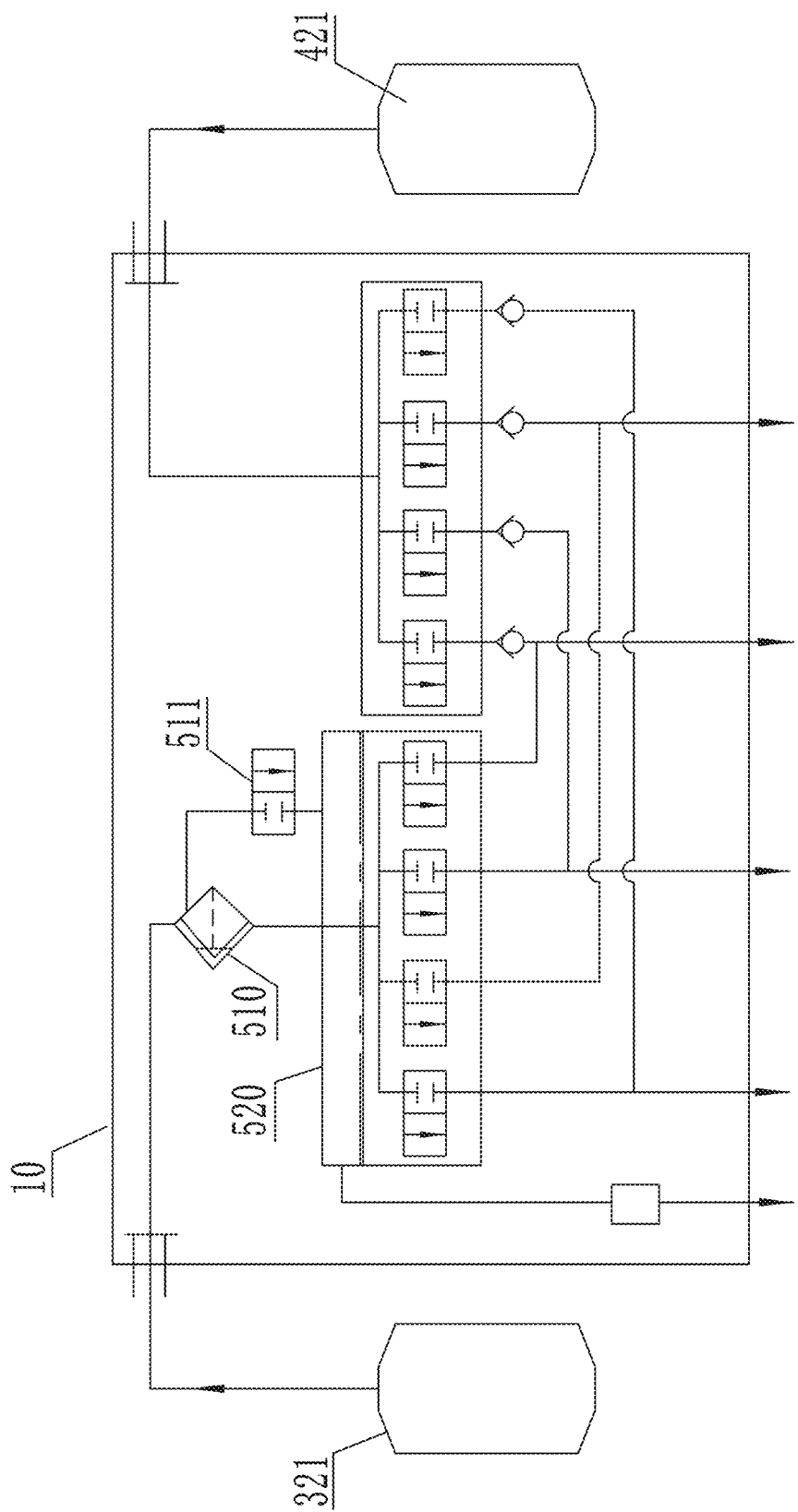
Figure 8:
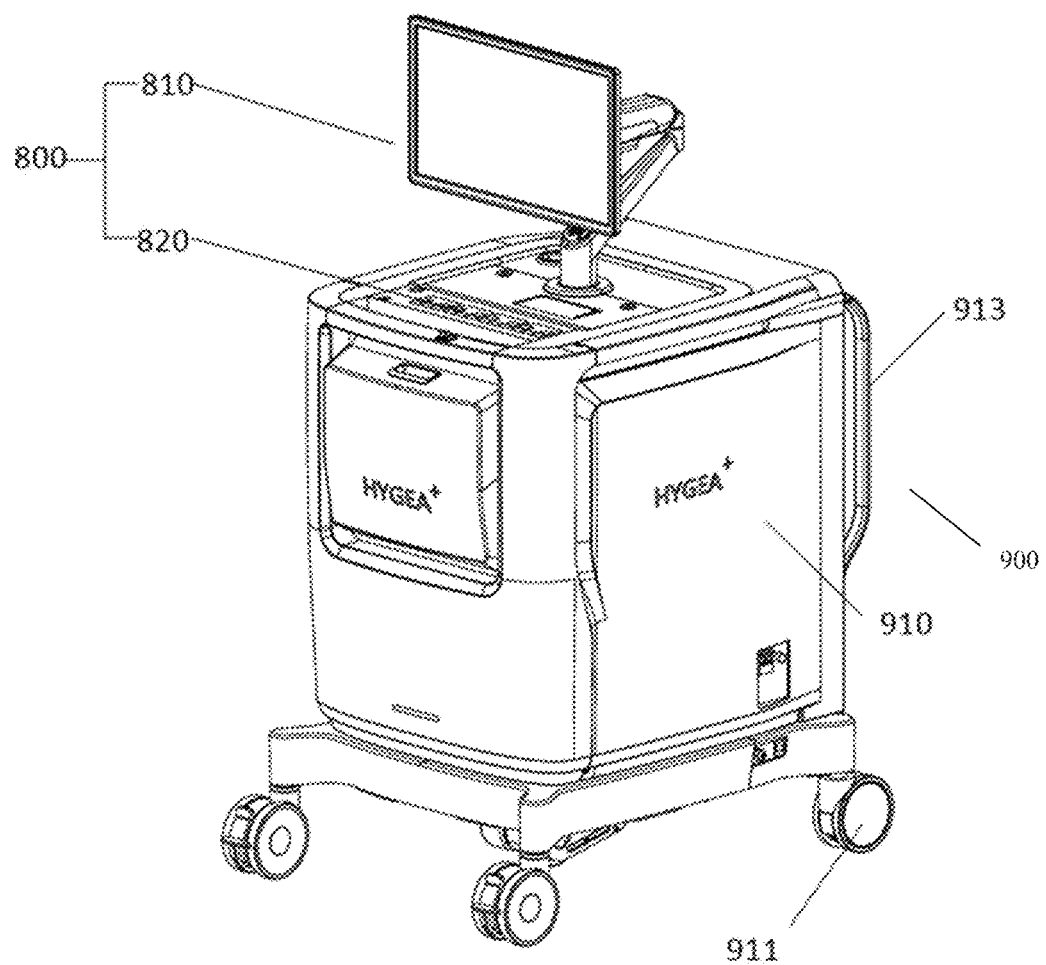
FIG. 8 and FIG. 9 schematically show a structure of a main unit according to an embodiment of the disclosure.
Figure 9:
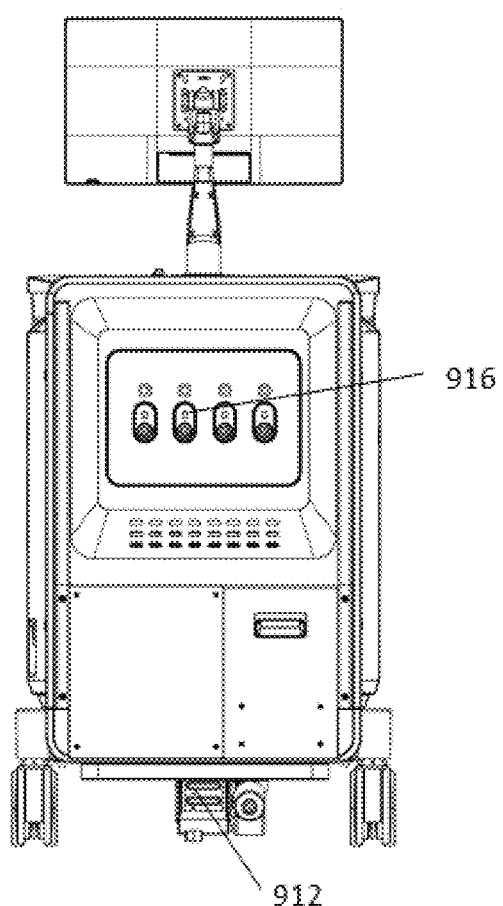
Figure 10:
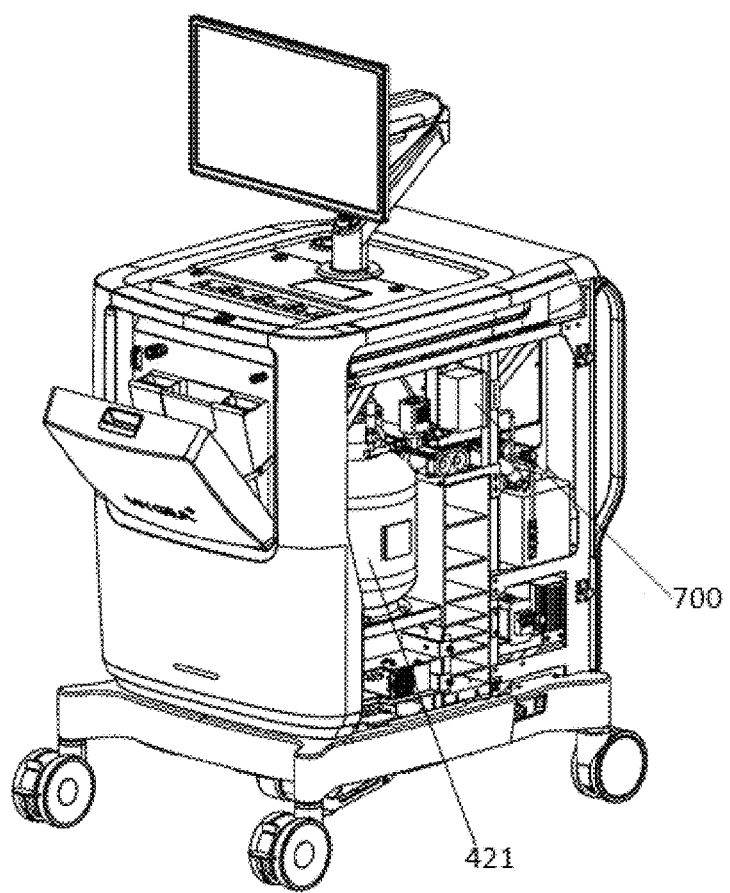
FIG. 10 and FIG. 11 schematically show a structure of the main unit with part of the housing hidden according to an embodiment of the disclosure.
Figure 11:
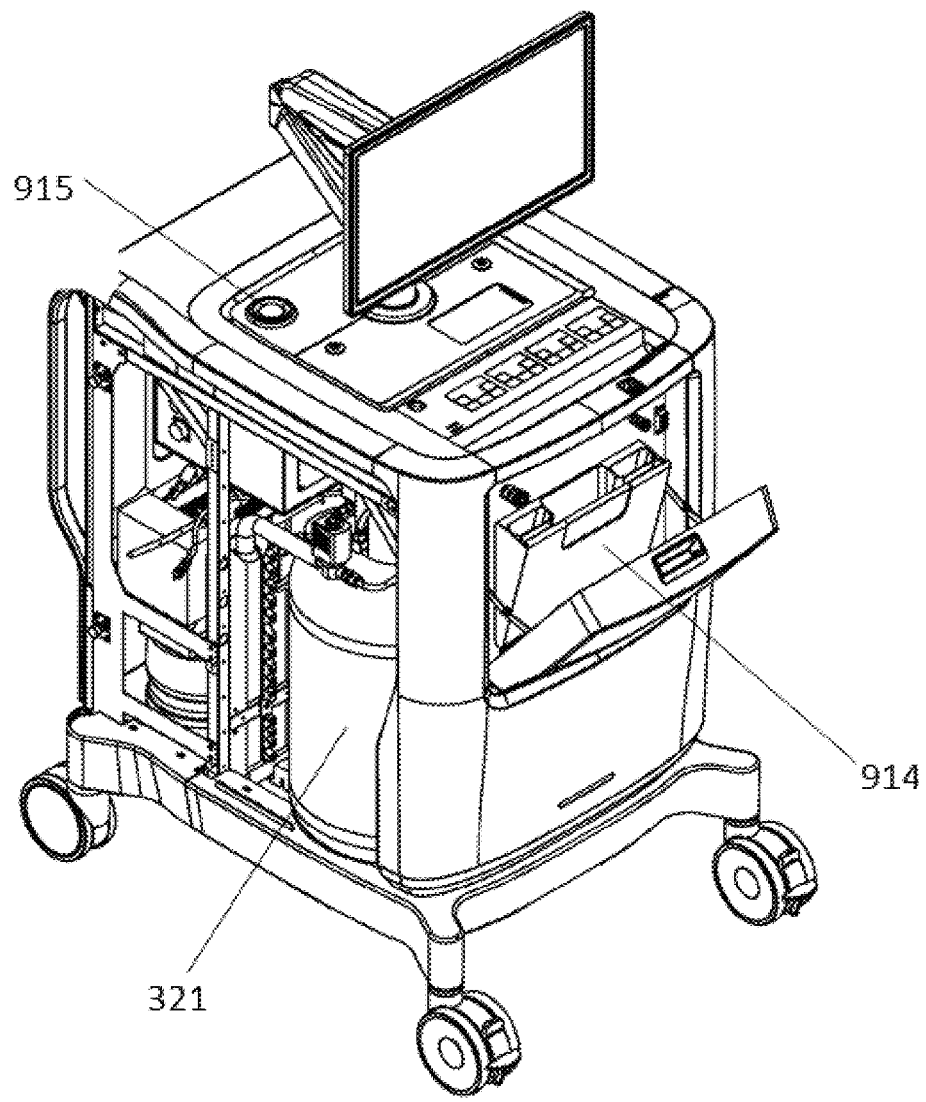
Figure 12:
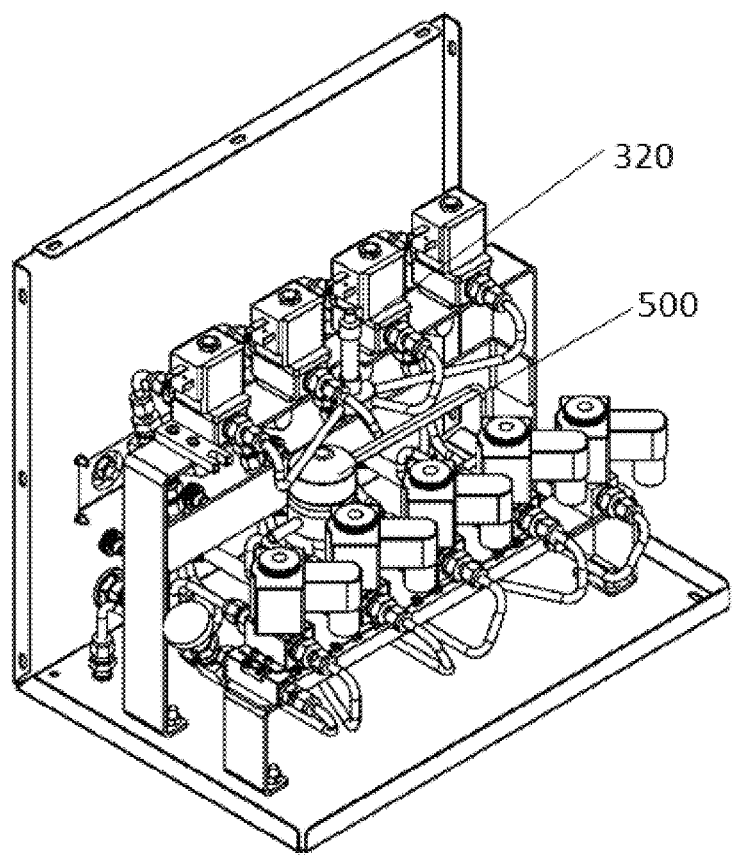
FIG. 12 schematically shows connection of pipelines in the working medium distribution system according to an embodiment of the disclosure.

In addition, as shown in FIG. 5, a temperature sensor is provided at an inlet of the working medium feeding pipe 201, and a temperature sensor is also provided at an outlet of the working medium backflow pipe 202, so as to detect the temperature of the working medium.

The high and low temperature composite ablation surgery system in the disclosure may adopts a working pressure that is below a critical point of the working medium. If the temperature is low enough at the same time, the working medium is liquid; and if the temperature is high enough at the same time, the working medium is gaseous. It can be understood that, a working pressure that is above the critical point of the working medium may also be adopted, and at this time the working medium is in a supercritical state.

Description is made by taking the working medium being nitrogen as an example.

A critical temperature of nitrogen $Tc=126.2K$ ($-147°$ C.), and a critical pressure $Pc=3.4$ MPa, a critical density being 313.3 kg/m$^3$. Nitrogen, around a critical point, has an unusually large coefficient of thermal expansion, an unusually large specific heat capacity, and a relatively small viscosity, and a relatively high heat exchange coefficient can be obtained when the temperature difference is small. In a process of delivering supercritical nitrogen, since the temperature is higher than the temperature of liquid nitrogen, there is small loss of cold energy along the way. Since nitrogen has a large working pressure, a relatively high density on the whole, and a relatively large mass flow rate, nitrogen is used as the cold working medium preferably in the disclosure.

A flowing path of the cold working medium in the disclosure is as follows.

The cold working medium in the cold working medium storage tank 311 sequentially passes through the discharging valve 312, perfusion interface 314, the liquid adding valve 315, and the one-way valve 316, and enters the cold tank 321 to complete liquid adding.

The cold working medium in the cold tank 321 is delivered into the cryogenic-thermal ablation probe 200 along a main pipeline for performing the therapy, and is delivered into the heat exchanger 610 along a branch pipeline for recycling.

Specifically, the cold working medium in the cold tank 321 sequentially passes through the discharging valve, the phase separator 510 and the precooler 520 along the main pipeline and enters the probe delivery pipe 210, and then enters the cryogenic-thermal ablation probe 200 through a feeding port of the cryogenic-thermal ablation probe 200. The cold working medium entering the cryogenic-thermal ablation probe 200 returns to a discharging port thereof after completing the therapy in the therapy area. The cold working medium at the discharging port of the cryogenic-thermal ablation probe 200 enters the heat exchanger 610 and is warmed, and the warmed cold working medium is discharged after being treated.

The cold working medium (which is gaseous) in the cold tank 321 passes through the manually operated valve 327 or the gas releasing valve 328 along the branch pipeline and enters the heat exchanger 610 for overpressure relief.

A flowing path of the hot working medium in the disclosure is as follows.

The hot working medium in the hot working medium storage tank 411 sequentially passes through the liquid adding opening 412, the perfusion pump 413, and the perfusion valve 414 and enters the hot tank 421 to complete liquid adding.

The hot working medium in the hot tank 421 is delivered into the cryogenic-thermal ablation probe 200 along a main pipeline for performing the therapy, and is delivered into the heat exchanger 610 along a branch pipeline for recycling.

Specifically, the hot working medium in the hot tank 421 sequentially passes through the discharging valve, the phase separator 510 and the precooler 520 along the main pipeline and enters the probe delivery pipe 210, and then enters the cryogenic-thermal ablation probe 200 through a feeding port of the cryogenic-thermal ablation probe 200. The hot working medium entering the cryogenic-thermal ablation probe 200 returns to a discharging port thereof after completing the therapy in the therapy area. The hot working medium at the discharging port of the cryogenic-thermal ablation probe 200 enters the heat exchanger 610 and is cooled, and the cooled hot working medium enters the recycling tank 620.

The hot working medium (which is under overpressure) in the hot tank 421 passes through the manually operated valve 428 or the gas releasing valve 429 along the branch pipeline and enters the heat exchanger 610 for recycling.

Although the present disclosure has been described with reference to preferred embodiments, various improvements can be made thereto and a component therein can be replaced with an equivalent without departing from the scope of the present disclosure. In particular, respective technical features mentioned in various embodiments can be combined in any manner as long as there is no structural conflict. The present disclosure is not limited to specific embodiments disclosed herein, but covers all the technical solutions falling within the scope of the appended claims.

The invention claimed is:

1. A high and low temperature composite ablation surgery system, comprising a main unit (100) and a cryogenic-thermal ablation probe (200) connected to the main unit (100), wherein the cryogenic-thermal ablation probe (200) is configured to perform therapy on a focus portion of a patient; and the main unit (100) comprises:
a cold working medium supply system (300), which is configured to deliver a cold working medium to the cryogenic-thermal ablation probe (200);
a hot working medium supply system (400), which is configured to deliver a hot working medium to the cryogenic-thermal ablation probe (200);
a working medium distribution system (500), which is connected to the cold working medium supply system (300) and the hot working medium supply system (400) respectively, and is configured to control the cold working medium supply system (300) to deliver the cold working medium to the cryogenic-thermal ablation probe (200) or control the hot working medium supply system (400) to deliver the hot working medium to the cryogenic-thermal ablation probe (200),
a recycling system (600), which is connected to a discharging port of the cryogenic-thermal ablation probe (200), the cold working medium supply system (300), and the hot working medium supply system (400) respectively; and
an electrical control system (700) comprising a computer control system;
wherein the hot working medium supply system (400) comprises a hot working medium automatic perfusion system (410) and a hot working medium pressure control system (420),
the hot working medium automatic perfusion system (410) comprising hot working medium storage tank (411),
the hot working medium pressure control system (420) comprising a hot tank (421) for bearing the hot working medium, wherein the hot tank (421) is configured to deliver the hot working medium under pressure to the cryogenic-thermal ablation probe (200),
wherein the hot working medium storage tank (411) and the hot tank (421) are connected by a pipeline, so as to deliver the hot working medium in the hot working medium storage tank (411) to the hot tank (421),
wherein the hot tank (421) is provided with a heating device, wherein the hot tank (421) is heated by the heating device, so that the hot working medium in the hot tank (421) generates vapor, so that the pressure is increased,
wherein the hot tank (421) is connected to the recycling system (600) by pipeline, wherein a safety valve (425), a pressure sensor (426), a pressure gauge (427), and a manually operated valve (428) are provided sequentially in series on the pipeline, wherein the manually operated valve (428) and a gas releasing valve (429) are connected in parallel,
wherein the pressure sensor (426) collects signals of pressure in the hot tank (421), and the computer control system is in communication with the pressure sensors (426) to monitor the pressure in the hot tank (421) in real time, wherein the gas releasing valve (429) is opened when the pressure in the hot tank (421) exceeds a working pressure.

2. The high and low temperature composite ablation surgery system according to claim 1, wherein the working medium distribution system (500) comprises:
a phase separator (510), which is connected to the cold working medium supply system (300); and
a precooler (520), which is provided with a gas channel (521) and a liquid channel, wherein a feeding side of the gas channel (521) is in communication with a gas outlet end of the phase separator (510), and a feeding side and a discharging side of the liquid channel are respectively in communication with a liquid outlet end of the phase separator (510) and the cryogenic-thermal ablation probe (200),
wherein gas in the gas channel (521) is used to precool liquid in the liquid channel.

3. The high and low temperature composite ablation surgery system according to claim 2, wherein the gas channel (521) is configured to be a channel having a maze shape.

4. The high and low temperature composite ablation surgery system according to claim 1, wherein the recycling system (600) comprises a heat exchanger (610), wherein the heat exchanger (610) is connected to the discharging end of the cryogenic-thermal ablation probe (200), and the heat exchanger (610) is configured to cool the hot working medium discharged by the cryogenic-thermal ablation probe (200) and recycle the hot working medium cooled.

5. The high and low temperature composite ablation surgery system according to claim 1, wherein the cold working medium supply system (300) comprises a cold working medium automatic perfusion system (310) and a cold working medium pressure control system (320),
the cold working medium automatic perfusion system (310) comprising a cold working medium storage tank (311),
the cold working medium pressure control system (320) comprising a cold tank (321) for bearing the cold working medium, wherein the cold tank (321) is configured to deliver the cold working medium under pressure to the cryogenic-thermal ablation probe (200),
wherein the cold working medium storage tank (311) and the cold tank (321) are connected by a pipeline, so as to deliver the cold working medium in the cold working medium storage tank (311) to the cold tank (321).

6. The high and low temperature composite ablation surgery system according to claim 5, wherein the cold tank (321) is connected with a pressurization pipeline (322), and two ends of the pressurization pipeline (322) are respectively connected to the cold tank (321) so as to form a closed loop, wherein the pressurization pipeline (322) is configured to allow the cold working medium in the cold tank (321) to realize self-pressurization.

7. The high and low temperature composite ablation surgery system according to claim 1, wherein the main unit (100) further comprises an interaction system (800) electrically connected to the electrical control system (700), wherein the electrical control system (700) is electrically connected to the cold working medium supply system (300), the hot working medium supply system (400) and the working medium distribution system (500) respectively, so as to control a working process of the working medium.

8. The high and low temperature composite ablation surgery system according to claim 6, wherein the cold tank (321) is further connected to the recycling system 600, and a gas releasing valve (328) is provided on a pipeline for releasing the pressure from the cold tank (321) to the recycling system (600), wherein the pressurization pipeline (322) is provided with a pressurization valve (323), and when the pressurization valve (323) is opened, the working medium in the cold tank (321) enters the pressurization pipeline (322), such that the cold working medium in the cold tank (321) can realize self-pressurization.

9. The high and low temperature composite ablation surgery system according to claim 2, wherein the precooler (520) includes an upper plate (522) and a lower plate (523), wherein the gas channel (521) is provided on the lower plate (523), liquid channels are provided in the upper plate (522) and the lower plate (523), wherein the gas channel (521) can cover at least a portion of the liquid channel.

10. The high and low temperature composite ablation surgery system according to claim 1, wherein the main unit (100) further comprises a power assisting system (900) comprising a power assisting wheel (911), an electrically controlled wheel (912), a lithium battery, and a handle (913), which are provided on a housing (910), wherein the power assisting wheel (911) provides power for movement of the main unit (100), the electrically controlled wheel (912) is configured to automatically lock the housing (910) when the housing (910) stops moving, and the handle (913) is integrated with a torque sensor.

* * * * *